United States Patent
Herzog et al.

(10) Patent No.: US 8,182,680 B2
(45) Date of Patent: May 22, 2012

(54) PRIMARY PISTON CORRECTION DURING TRANSFER

(75) Inventors: Philip Herzog, Waldbronn (DE); Konstantin Choikhet, Waldbronn (DE); Klaus Witt, Waldbronn (DE); Herbert Anderer, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 353 days.

(21) Appl. No.: 12/431,972

(22) Filed: Apr. 29, 2009

(65) Prior Publication Data

US 2010/0275678 A1 Nov. 4, 2010

(51) Int. Cl.
*B01D 15/08* (2006.01)

(52) U.S. Cl. ........ 210/198.2; 96/156; 210/101; 210/656; 210/741; 73/61.56; 417/2; 417/44.2; 417/63; 417/265; 422/70; 436/161

(58) Field of Classification Search ............... 210/101, 210/103, 137, 188, 198.2, 656, 739, 741; 417/2–6, 18, 20, 36, 38, 43, 44.2, 44.3, 44.8, 417/17, 212, 213, 254, 265, 53, 426; 73/61.52, 73/61.56; 96/155, 156; 436/161
See application file for complete search history.

(56) References Cited

U.S. PATENT DOCUMENTS

| | | | | |
|---|---|---|---|---|
| 4,137,011 A | * | 1/1979 | Rock | 417/22 |
| 4,556,367 A | * | 12/1985 | Schmid | 417/18 |
| 4,681,513 A | * | 7/1987 | Saito et al. | 417/2 |
| 4,808,077 A | | 2/1989 | Kan et al. | |
| 4,883,409 A | * | 11/1989 | Strohmeier et al. | 417/43 |
| 5,108,264 A | * | 4/1992 | Abdel-Rahman | 417/20 |
| 5,457,626 A | * | 10/1995 | Wolze | 700/32 |
| 5,620,524 A | * | 4/1997 | Fan et al. | 118/726 |
| 6,068,448 A | * | 5/2000 | Muratsubaki et al. | 417/44.2 |
| 6,923,916 B1 | | 8/2005 | Hiraku et al. | |
| 7,631,542 B2 | * | 12/2009 | Weissgerber | 73/61.56 |
| 7,850,844 B2 | * | 12/2010 | Kaji et al. | 210/198.2 |
| 2005/0061722 A1 | * | 3/2005 | Takao et al. | 210/137 |
| 2006/0219618 A1 | | 10/2006 | Witt et al. | |
| 2007/0000312 A1 | * | 1/2007 | Weissgerber | 73/61.56 |
| 2007/0084766 A1 | | 4/2007 | Ishii et al. | |
| 2009/0193879 A1 | * | 8/2009 | Yasuhara et al. | 73/61.56 |

FOREIGN PATENT DOCUMENTS

| | | |
|---|---|---|
| EP | 0367099 A2 | 5/1990 |
| GB | 2189555 A1 | 10/1987 |
| WO | 2006017121 A2 | 2/2006 |

* cited by examiner

*Primary Examiner* — Joseph Drodge
(74) *Attorney, Agent, or Firm* — Volentine & Whitt, PLLC

(57) ABSTRACT

A method for controlling operation of a pump unit, where the pump unit includes a primary piston pump having a primary piston and a secondary piston pump having a secondary piston. The primary piston pump is fluidically connected with the secondary piston pump. The primary piston pump includes an inlet valve and an outlet valve, and the pump unit operates periodically according to a pump cycle. The method includes determining a fluid pressure of fluid dispensed by the pump unit, and performing a closed loop control of a position of the primary piston in dependence on the fluid pressure of the fluid dispensed by the pump unit during a first time interval of the pump cycle.

19 Claims, 6 Drawing Sheets

PRIMARY PISTON CORRECTION DURING TRANSFER

BACKGROUND

The disclosed embodiments relate to a method for controlling operation of a pump unit. The present invention further relates to a pump unit, and to a fluid separation system for separating compounds of a sample fluid in a mobile phase.

U.S. patent application 2006/0219618 A1 relates to solvent supply with a correction of piston movement.

International patent application WO 2006017121 describes a feedback control loop for a high pressure pump that modifies the accumulator velocity and pressure during solvent transfer. The accumulator velocity is adjusted to maintain the system pressure equal to the expected pressure to thereby eliminate the effect of the flow deficit created by a thermal effect.

SUMMARY

It is an object of the invention to provide an improved operation of a pump unit comprising a primary piston pump fluidically connected with a secondary piston pump. The object is solved by the independent claim(s). Further embodiments are shown by the dependent claim(s).

According to embodiments of the present invention, a method for controlling operation of a pump unit is proposed, the pump unit comprising a primary piston pump having a primary piston and a secondary piston pump having a secondary piston. The primary piston pump is fluidically connected with the secondary piston pump. The primary piston pump comprises an inlet valve and an outlet valve, and the pump unit operates periodically according to a pump cycle comprising a deliver-and-fill phase for delivering fluid from the primary piston pump to the secondary piston pump and to a fluidic system located downstream of the pump unit. The method comprises determining a fluid pressure of fluid dispensed by the pump unit, and—during a first time interval of the pump cycle—performing a closed loop control of a position of the primary piston in dependence on the fluid pressure of the fluid dispensed by the pump unit, while a predefined position-versus-time curve is performed by the secondary piston. The first time interval corresponds to the deliver-and-fill phase.

During the first time interval, the closed loop control is applied to the primary piston pump. Accordingly, during the first time interval, corrective movements are superimposed onto the primary piston's movement.

Superposing corrective movements onto the primary piston's movement leads to a number of advantages. First of all, by applying the closed loop control to the primary piston pump, various errors are compensated at the location where they occur, i.e. at the primary piston pump.

For example, a compression stroke may be performed by the primary piston, According to embodiments of the present invention, in case the compression stroke is too short, an additional downward movement is applied to the primary piston. By applying the additional downward movement to the primary piston, the error is counteracted at the location where it has occurred, i.e. at the primary piston pump. As a result, a continuous prolonged downward movement of the primary piston is obtained.

Also with regard to thermal fluctuations that may lead to volumetric errors, it is proposed to counteract these thermal effects at the location where they occur, i.e. at the primary piston pump. Thus, undesired effects related to temperature fluctuations are kept as small as possible. For this reason, during the first time interval, the closed loop control is applied to the primary piston pump.

Furthermore, when imposing a corrective movement onto the primary piston pump, any discontinuity of flow related to this correction is dampened when passing the fluid from the primary piston pump to the pump system's outlet. The primary piston pump is located upstream of the secondary piston pump, and therefore, the fluid has to pass the additional flow path between the primary piston pump and the secondary piston pump before reaching the pump system's outlet. This additional hydraulic capacitance is sufficiently large to dampen any discontinuity of flow and pressure that occurs when applying a correction onto the primary piston pump's piston movement.

As another advantage, when the closed loop control is applied to the primary piston pump during the first time interval, and not to the secondary piston pump, it is much easier to maintain synchronization between the piston movement of the primary piston pump and the piston movement of the secondary piston pump. The secondary piston pump is permanently exposed to system pressure, and therefore, any correction applied to the secondary piston's movement may affect the pump cycle of the secondary piston pump. In contrast, the primary piston pump is alternatingly coupled to and decoupled from system pressure. In case a corrective movement is superimposed onto the primary piston's movement when the primary piston pump is coupled to system pressure, the corrective movement may also effect the period of time needed for a respective phase of the primary piston pump's operation. However, during the periods of time when the primary piston pump is decoupled from system pressure, the effects imposed onto the timing of the primary piston pump's operation may be compensated for. For this reason, it is possible to maintain a constant pump cycle even in case corrective movements are applied to the primary piston's movement. In this regard, the corrections applied to the piston movement of the primary piston pump do not disturb the synchronization between the primary piston pump and the secondary piston pump. A correction applied to the secondary piston pump would be much more critical in terms of disturbing the synchronization between the two piston pumps.

During the first time interval, the closed loop control of the position of the primary piston is performed while a predefined position-versus-time curve is performed by the secondary piston. Hence, during the first time interval, the closed loop control is solely applied to the primary piston pump.

According to a preferred embodiment, the primary piston pump is configured for delivering, during the first time interval, fluid to the secondary piston pump and to a fluidic system located downstream of the pump unit.

According to a preferred embodiment, the first time interval is said deliver-and-fill phase. As long as the primary piston pump delivers fluid to the secondary piston pump and to the fluidic system located downstream of the pump unit, the corrective movements are superimposed onto the primary piston's movement. Thus, any pressure discontinuities are counteracted at the location where they occur.

According to a preferred embodiment, performing the closed loop control of the primary piston's position comprises determining a first position correction signal for imposing, during the first time interval, a corrective movement onto a regular piston movement of the primary piston.

According to a preferred embodiment, performing the closed loop control of the primary piston's position comprises determining a variance between the fluid pressure of the fluid dispensed by and the pump unit and a predetermined target pressure, and deriving, from said variance, a first position correction signal for imposing, during the first time interval, a corrective movement onto a regular piston movement of the primary piston. As an outcome of the closed loop control, the fluid pressure of the fluid dispensed by the pump unit is driven towards the predetermined target pressure.

According to a preferred embodiment, performing the closed loop control of the primary piston's position comprises determining a first position correction signal for imposing, during the first time interval, a corrective movement onto a regular piston movement of the primary piston, and applying, during the first time interval, the first position correction signal to the primary piston pump.

According to a preferred embodiment, during the first time interval, in case the fluid pressure of the fluid dispensed by the pump unit is too small, movement of the primary piston is corrected by superimposing a forward movement onto the primary piston, and in case the fluid pressure of the fluid dispensed by the pump unit is too large, movement of the primary piston is corrected by superimposing a backward movement onto the primary piston.

According to a preferred embodiment, the pump cycle further comprises at least one of: an intake phase for drawing fluid into the primary piston pump; an inlet valve settle phase for closing the inlet valve of the primary piston pump; a compression phase for bringing a fluid contained in the primary piston pump to system pressure; an outlet valve settle phase for closing the outlet valve of the primary piston pump; a decompression phase for bringing a fluid remaining in the primary piston pump from system pressure to an initial pressure.

According to a preferred embodiment, during at least one second time interval of the pump cycle, which is different from the first time interval, a closed loop control of the secondary piston's position is performed in dependence on the fluid pressure of the fluid dispensed by the pump unit.

According to a preferred embodiment, during the at least one second time interval, the closed loop control of the position of the secondary piston is performed while a predefined position-versus-time curve is performed by the primary piston. Preferably, the at least one second time interval does not overlap substantially with the first time interval.

According to a preferred embodiment, the at least one second time interval does not substantially overlap with the deliver-and-fill phase. During the deliver-and-fill phase, the primary piston pump is responsible for supplying fluid at system pressure, and therefore, the closed loop control may e.g. be applied to the primary piston pump. In contrast, during the at least one second time interval, the primary piston pump's outlet valve may e.g. be closed, and the closed loop control may be applied to the secondary piston pump.

According to a preferred embodiment, the at least one second time interval includes at least one of: an intake phase for drawing fluid into the primary piston pump, an inlet valve settle phase for closing the inlet valve of the primary piston pump, a compression phase for bringing a fluid contained in the primary piston pump to system pressure, an outlet valve settle phase for closing the outlet valve of the primary piston pump, a decompression phase for bringing a fluid remaining in the primary piston pump from system pressure to an initial pressure. Any pressure discontinuity that occurs during any one of the above-mentioned phases may be counteracted by superposing a corresponding corrective movement onto the secondary piston's movement.

According to a preferred embodiment, during a subinterval of the pump cycle, said closed loop control is alternatingly applied to the primary piston pump and to the secondary piston pump. According to this embodiment, during the subinterval of the pump cycle, the closed loop control is switched between the primary and the secondary piston pump, in order to yield the best possible results with regard to stabilizing fluid pressure.

According to a preferred embodiment, during a subinterval of the pump cycle, said closed loop control is alternatingly applied to the primary piston pump and to the secondary piston pump, and during a remaining part of the pump cycle, said closed loop control is inactive. For example, during the secondary piston pump's delivery phase, it may not be required to perform any closed loop control of the piston movements.

According to a preferred embodiment, during the pump cycle, said closed loop control is alternatingly applied to the primary piston pump and to the secondary piston pump.

According to a preferred embodiment, at the beginning of the first time interval, the closed loop control is switched from controlling the secondary piston pump to controlling the primary piston pump. According to a further preferred embodiment, at the end of the first time interval, the closed loop control is switched from controlling the primary piston pump to controlling the secondary piston pump.

According to a preferred embodiment, during the first time interval, said closed loop control of the position of the primary piston is performed in a way that the fluid pressure of the fluid dispensed by the pump unit continues to follow its former trend. Thus, the fluid pressure of the fluid dispensed by the pump unit is stabilized.

According to a preferred embodiment, during the first time interval, said closed loop control of the primary piston's position is performed in a way that the fluid pressure of the fluid dispensed by the pump unit is driven towards or substantially kept at a predetermined target pressure.

Preferably, the target pressure is determined by performing an extrapolation of former values of the fluid pressure of the fluid dispensed by the pump unit.

Further preferably, the target pressure is determined by performing an extrapolation of former values of the fluid pressure of the fluid dispensed by the pump unit in a way that the fluid pressure of the fluid dispensed by the pump unit shows a continuous progression.

According to a preferred embodiment, the method further comprises deriving, from the closed loop control of the primary piston's position performed during the first time interval, at least one correction to be applied to a regular piston movement of at least one of the primary piston pump and the secondary piston pump. The corrections imposed onto the piston movements contain information about how the predefined regular piston movement should be modified to accomplish a stable pressure of the fluid dispensed by the pump unit. Therefore, the corrections can be used for modifying and improving the regular piston movement of at least one of the primary and the secondary piston pump.

According to a preferred embodiment, the method further comprises deriving, from the closed loop control of the primary piston's position performed during the first time interval, at least one of the following: a correction of the compression jump and a correction of the fluid's thermal expansion.

According to a preferred embodiment, the method further comprises deriving, from the closed loop control the primary piston's position performed during the first time interval, at least one correction to be applied to a regular piston movement of at least one of the primary piston pump and the secondary piston pump, with said at least one correction being used for modifying a regular piston movement of at least one of the primary piston pump and the secondary piston pump during subsequent pump cycles.

A pump unit according to embodiments of the present invention comprises: a primary piston pump with a primary piston and a secondary piston pump with a secondary piston, the primary piston pump being fluidically connected with the secondary piston pump, the primary piston pump comprising an inlet valve and an outlet valve, and the pump unit operating periodically according to a pump cycle comprising a deliver-and-fill phase for delivering fluid from the primary piston pump to the secondary piston pump and to a fluidic system located downstream of the pump unit. The pump unit comprises a pressure detection unit configured for determining a fluid pressure of fluid dispensed by the pump unit. Further, the pump unit comprises a control unit configured for performing, during a first time interval of the pump cycle, a closed loop control of a position of the primary piston in dependence on the fluid pressure of the fluid dispensed by the pump unit, while a predefined position-versus-time curve is performed by the secondary piston. The first time interval corresponds to the deliver-and-fill phase.

A fluid separation system for separating compounds of a sample fluid in a mobile phase according to embodiments of the present invention comprises a pump unit as described above, the pump unit being configured for driving the mobile phase through the fluid separation system, and a separation unit, preferably a chromatographic column, configured for separating compounds of the sample fluid in the mobile phase.

According to a preferred embodiment, the fluid separation system further comprises at least one of: a sample injector configured for introducing the sample fluid into the mobile phase; a detector configured for detecting separated compounds of the sample fluid; a collection unit configured for collecting separated compounds of the sample fluid; a data processing unit configured for processing data received from the fluid separation system; a degassing apparatus configured for degassing the mobile phase.

Embodiments of the invention can be partly or entirely embodied or supported by one or more suitable software programs or program code, which can be stored on or otherwise provided by any kind of computer readable storage medium, and which might be executed in or by any suitable data processing system. The computer readable storage medium may utilize optical, magnetic, chemical, electrical, or any other suitable properties for receiving, storing, or delivering instructions and commands, and may include magnetic media, such as a diskette, disk, memory stick or computer hard drive, which is readable and executable by a computer. In other embodiments, the computer readable storage medium may include optical disks, read-only-memory ("ROM") floppy disks and semiconductor materials and chips, or any suitable technology for implementing the embodiments disclosed herein. Software programs or routines can be preferably applied for controlling respective movements of at least one of the primary piston and the secondary piston.

BRIEF DESCRIPTION OF DRAWINGS

Other objects and many of the attendant advantages of embodiments of the present invention will be readily appreciated and become better understood by reference to the following more detailed description of embodiments in connection with the accompanied drawing(s). Features that are substantially or functionally equal or similar will be referred to by the same reference sign(s).

FIG. 4 indicates when the first position correction signal is active and when the second position correction signal is active;

DETAILED DESCRIPTION

Figure 1:
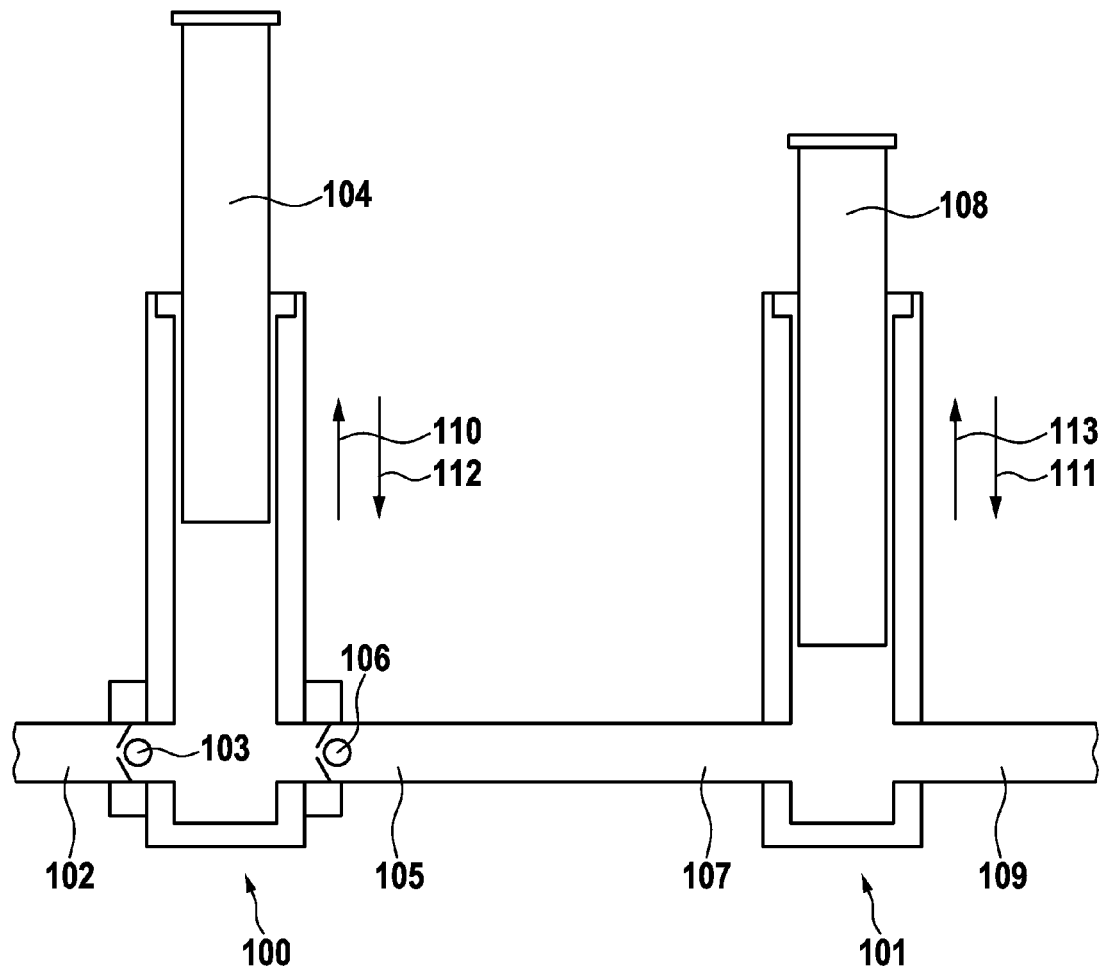
FIG. 1 shows a dual piston serial type pump comprising a primary piston pump and a secondary piston pump.

FIG. 1 shows a dual piston serial-type pump comprising a primary piston pump 100 that is fluidically connected in series with a secondary piston pump 101. The primary piston pump 100 comprises an inlet 102 with an inlet valve 103, a piston 104 that reciprocates in the primary piston pump 100, and an outlet 105 with an outlet valve 106. The outlet 105 is fluidically connected with an inlet 107 of the secondary piston pump 101. A piston 108 reciprocates in the secondary piston pump 101. The secondary piston pump 101 further comprises an outlet 109 for delivering a flow of fluid.

In the upper portion of FIG. 2, the primary piston's position p1 is depicted as a function of time, and in the lower portion of FIG. 2, right below the primary piston's position p1, the secondary piston's position p2 is shown as a function of time. During an intake phase 200 of the primary piston pump 100, the primary piston 104 performs an upward stroke, as indicated by arrow 110. The inlet valve 103 is opened, and fluid at atmospheric pressure is drawn into the primary piston pump 100.

During an inlet valve settle phase 201, the inlet valve 103 is closed. Then, starting at the point of time 202, the primary piston 104 performs a compression stroke 203 in the downward direction, as indicated by arrow 112, and the fluid contained in the primary piston pump 100 is compressed to a system pressure of several hundred or even more than thousand bar. During the compression phase 203, both the inlet valve 103 and the outlet valve 106 are closed.

At a point of time 204, the fluid contained in the primary piston pump 100 has reached system pressure, and the outlet valve 106 opens. In a subsequent delivery phase 205 of the primary piston pump 100, the primary piston 104 continues its downward movement, and a flow of fluid is dispensed at the outlet 105 of the primary piston pump 100. Accordingly, during a deliver-and-fill phase 206 indicated in the lower portion of FIG. 2, the flow of fluid provided by the primary piston pump 100 is supplied to the secondary piston pump 101 and to the fluidic system located downstream of the pump unit, and the secondary piston pump's pump chamber is filled up.

During the deliver-and-fill phase 206, fluid may e.g. be supplied to the secondary piston pump 101 at a flow rate of about 5 to 20 ml/min. As a consequence of this large resupply rate, the deliver-and-fill phase 206 can be quite short. In the examples shown in FIG. 2, the deliver-and-fill phase 206 only extends over a small portion of a pump cycle 211. For example, the deliver-and-fill phase may extend over less than 10% of the pump cycle.

At the point of time 207, the downward stroke of the primary piston 104 is finished, and during an outlet valve settle phase 208, the outlet valve 106 is closed. At the end of the primary piston's downward stroke, a certain dead volume of fluid remains in the pump chamber of the primary piston pump 100, said dead volume of fluid being at system pressure. To decompress this dead volume of fluid, the primary piston 104 performs a decompression stroke 209, which is a fast movement in the upward direction. At the point of time 210, the dead volume of fluid is approximately at atmospheric pressure, and the inlet valve 103 opens. Now, the pump cycle 211 is finished, and a new pump cycle 212 starts. During an intake phase 213 of the primary piston pump 100, the primary piston 104 performs an upward stroke, as indicated by arrow 110, and fluid at atmospheric pressure is drawn into the primary piston pump 100.

Figure 2:
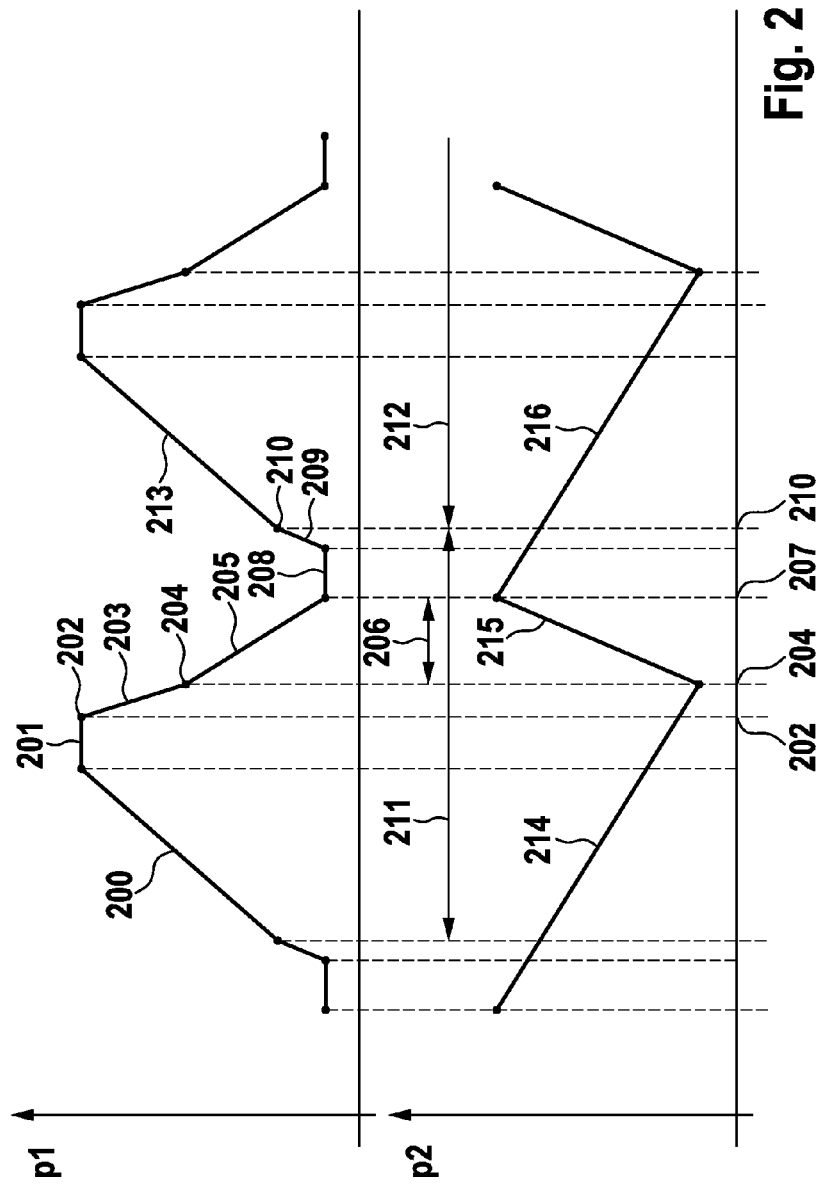
FIG. 2 shows the piston movements of the primary piston and the secondary piston as a function of time.

The lower portion of FIG. 2 shows the position p2 of the secondary piston pump's piston as a function of time. During a delivery phase 214 of the secondary piston pump 101, the secondary piston 108 performs a downward movement, as indicated by arrow 111, and dispenses a continuous flow of fluid at the outlet 109 of the secondary piston pump 101.

Then, at the point of time 204, the outlet valve 106 is opened. During an intake phase 215 of the secondary piston pump 101, the secondary piston 108 performs an upward stroke, as indicated by arrow 113, and draws in fluid supplied by the primary piston pump 100. During the intake phase 215, the flow of fluid supplied by the primary piston pump 100 is partly used for filling up the fluid chamber of the secondary piston pump 101 and partly used for maintaining a continuous flow of fluid at the outlet 109. At the point of time 207, the pump chamber of the secondary piston pump 101 is filled with fluid. Then, during a subsequent delivery phase 216, the secondary piston 108 performs a downward stroke, as indicated by arrow 111, and a flow of fluid is dispensed at the outlet 109.

The primary piston pump 100 and the secondary piston pump 101 may e.g. perform predefined regular piston movements as shown in FIG. 2. The pump system may e.g. comprise an actuation mechanism for operating the primary and the secondary piston in accordance with these predefined piston movements. However, especially in the time interval around the deliver-and-fill phase 206, the flow of fluid dispensed by the pump system may fluctuate, and accordingly, the pressure at the outlet may be subjected to fluctuations as well.

To counteract these fluctuations observed at the pump system's outlet and to stabilize pressure and flow of the dispensed fluid, corrective movements are superimposed onto at least one of the predefined regular piston movements shown in FIG. 2. According to embodiments of the present invention, a closed loop control is set up for controlling at least one of the piston movements in accordance with a fluid pressure detected at the pump system's outlet. The pressure at the outlet may e.g. be compared with a predefined setpoint value indicating a target pressure. In case the actual pressure is too small, an additional forward displacement may be imposed onto at least one of the primary and the secondary piston's movement. In case the pressure detected at the outlet is too large, an additional backward displacement may be imposed onto at least one of the primary and the secondary piston's movement. By adaptively controlling the piston positions in accordance with a closed loop control, fluid pressure at the outlet of the pump system is stabilized, and fluctuations of fluid pressure are reduced.

Figure 3:
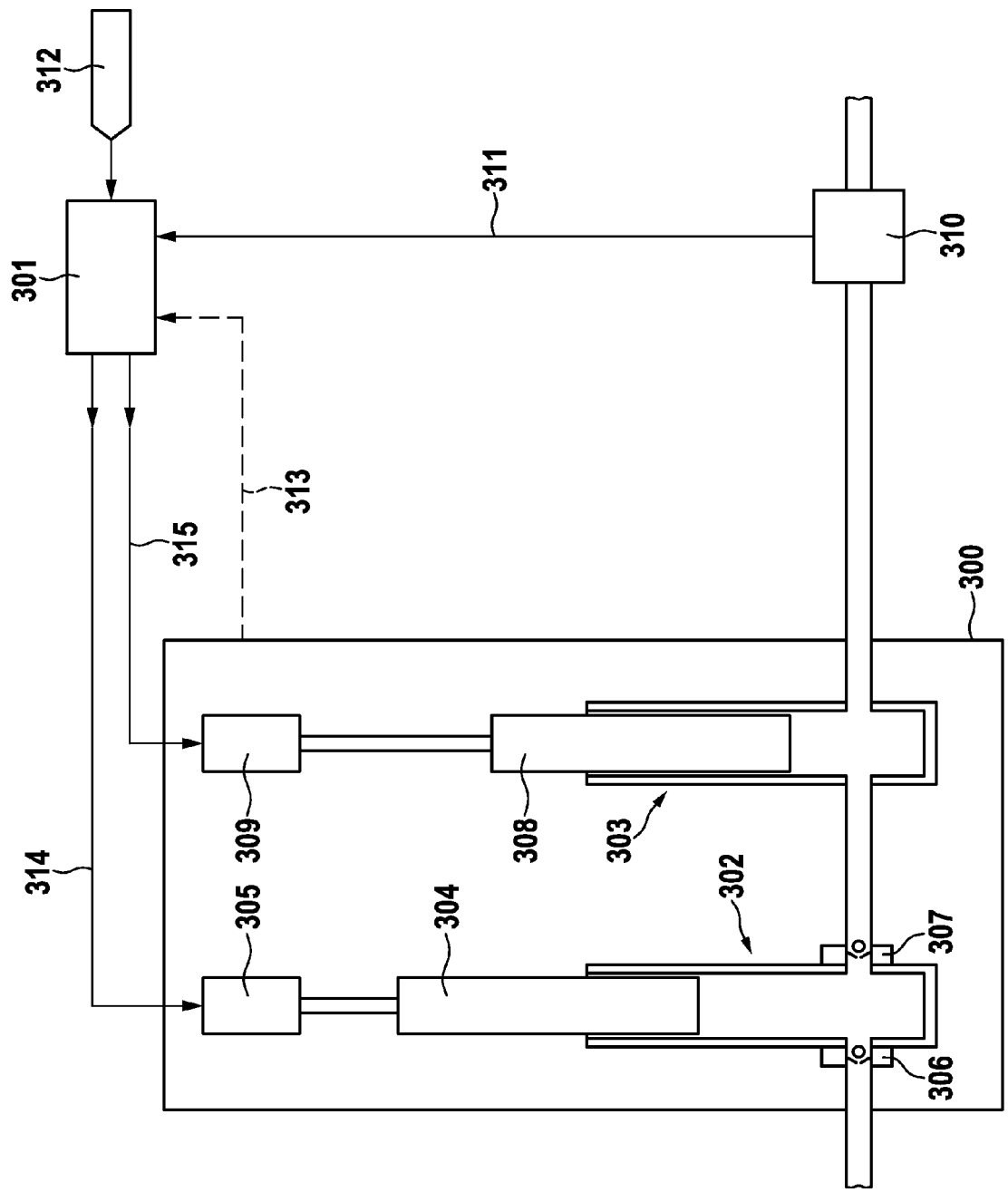
FIG. 3 shows a set up of a pump system according to embodiments of the present invention.

FIG. 3 shows a pump system according to embodiments of the present invention. The pump system comprises a pump unit 300 and a control unit 301 adapted for performing a closed loop control of the pump unit's operation. The pump unit 300 comprises a primary piston pump 302 that is fluidically connected in series with a secondary piston pump 303. The primary piston pump comprises a primary piston 304, the primary piston 304 being driven by a first actuator mechanism 305. The primary piston pump 302 further comprises an inlet valve 306 and an outlet valve 307. The secondary piston pump 303 comprises a secondary piston 308, the secondary piston 308 being driven by a second actuator mechanism 309.

The pressure of the fluid dispensed by the pump unit 300 is determined by a pressure detection unit 310 located downstream of the pump unit 300. The actual pressure value 311 determined by the pressure detection unit 310 is forwarded to the control unit 301. There, the actual pressure value 311 is compared with a setpoint value 312 that indicates a desired target pressure. The setpoint value 312 may for example be obtained by extrapolating a plurality of former pressure values. The control unit 301 may further receive phase information 313 indicating a phase of operation of the first actuator mechanism 305 and/or of the second actuator mechanism 309.

The control unit 301 is configured to determine, based on the variance between the actual pressure value 311 and the setpoint value 312, at least one position correction signal for imposing a corrective movement onto a regular piston movement of at least one of the pistons 304 and 308. In the embodiment shown in FIG. 3, two position correction signals 314, 315 are generated, the first position correction signal 314 being provided to the first actuator mechanism 305, and the second position correction signal 315 being provided to the second actuator mechanism 309. The corrective movements imposed onto the regular piston movements are chosen such that the fluid pressure at the outlet of the pump system is driven towards the target pressure indicated by the setpoint value 312. Thus, the fluid pressure at the outlet of the pump system is stabilized.

The closed loop control shown in FIG. 3 does not have to be active during the entire pump cycle. For example, during the intake phases 200, 213 of the primary piston pump, the secondary piston pump dispenses a steady flow of fluid. During the intake phases 200, 213 of the primary piston pump, the flow of fluid obtained at the pump system's outlet is quite stable. Therefore, during these intervals of the pump cycle, it is not necessary to perform a closed loop control of output pressure.

According to preferred embodiments of the present invention, during a pump cycle, position correction signals are alternatingly applied to the piston movement of the primary piston 304 and to the piston movement of the secondary piston 308. For example, during the compression phase 203 shown in the upper portion of FIG. 2, the second position correction signal 315 may be active. Hence, during the compression phase 203, a corrective movement is imposed onto the movement of the secondary piston 308, whereas the primary piston 304 performs a predefined regular piston movement.

At the point of time 204, the outlet valve 307 of the primary piston pump is opened, the primary piston pump 302 starts dispensing fluid, and the closed loop control is switched from the secondary piston 308 to the primary piston 304. During the deliver-and-fill phase 206, corrective piston movements are solely applied to the primary piston 304, while the secondary piston 308 performs a predefined regular movement.

At the point of time 207, the deliver-and-fill phase 206 is terminated, and the closed loop control is switched back from the primary piston 304 to the secondary piston 308. During the outlet valve settle phase 208 and the decompression phase 209, the closed loop control is solely applied to the secondary piston 308, while the primary piston 304 performs a predefined regular movement.

At the point of time 210, the decompression phase 209 is finished, and the primary piston's intake phase 213 is started. During the primary piston's intake phase 213, a steady flow of fluid is dispensed by the secondary piston pump, and hence, no closed loop control of the piston movement is necessary. Therefore, according to a preferred embodiment of the present invention, the closed loop control of the secondary piston's movement is switched off at the point of time 210, or right after the point of time 210.

Hence, according to a preferred embodiment of the present invention, the closed loop control is switched back and forth between the primary piston pump 302 and the secondary piston pump 303. According to a further preferred embodiment, the closed loop control is only active during a subinterval of a pump cycle.

In FIG. 4, which is located right below FIG. 2, it is indicated when the first position correction signal 314 is active, and when the second position correction signal 315 is active. During the compression phase 203, the second position correction signal 315 is active, which is indicated by a hatched segment 400. Then, at the point of time 204, the closed loop control is switched from the secondary piston pump 303 to the primary piston pump 302. During the deliver-and-fill phase 206, the second position correction signal 315 is inactive, and the first position correction signal 314 is active, which is indicated by the hatched segment 401. Then, at the point of time 207, the closed loop control is switched back from the primary piston pump 302 to the secondary piston pump 303. Hence, the first position correction signal 314 becomes inactive, whereas the second position correction signal 315 is activated, as indicated by the hatched segment 402. Hence, during the outlet valve settle phase 208 and the decompression phase 209 of the primary piston pump, the closed loop control is applied to the secondary piston pump. Then, during the intake phase 213 of the primary piston pump, both the first position correction signal 314 and the second position correction signal 315 are inactive, and no corrective movements are superimposed onto the regular piston movements of the primary piston 304 and the secondary piston 308.

Figure 5:
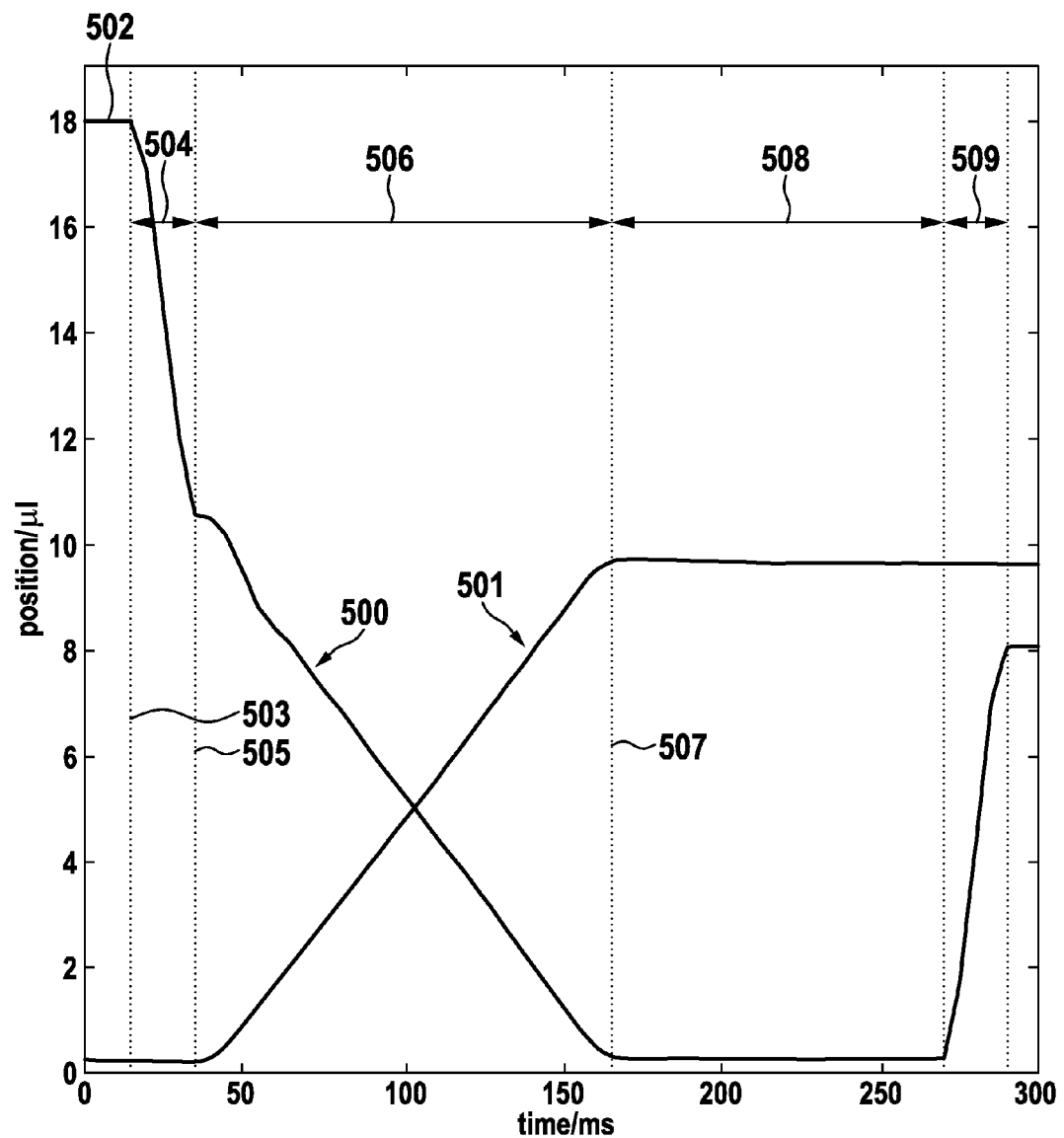
FIG. 5 shows position-versus-time curves for the primary and the secondary piston.

FIG. 5 depicts both the position vs. time curve 500 of the primary piston pump and the position vs. time curve 501 of the secondary piston pump for a subinterval of the pump cycle in which the closed loop control of the pump system is active.

During the inlet valve settle phase 502, the closed loop control is not active yet. At the point of time 503, the closed loop control of the secondary piston pump is started. During the compression phase 504, the outlet valve of the primary piston pump is still closed, and the volume of fluid contained in the primary piston pump is compressed to system pressure. During the compression phase 504, the closed loop control is applied to the secondary piston.

Then, at the point of time 505, the outlet valve of the primary piston pump opens, and the closed loop control is switched from the secondary piston pump to the primary piston pump. During the deliver-and-fill phase 506, the closed loop control is applied to the primary piston pump. During the deliver-and-fill phase 506, the primary piston pump supplies a flow of fluid to the secondary piston pump and to the fluidic system located downstream of the pump unit, and the volume of fluid is taken in by the secondary piston pump.

At the point of time 507, the deliver-and-fill phase 506 is finished, and the closed loop control is transferred from the primary piston pump back to the secondary piston pump.

During the outlet valve settle phase 508 and the decompression phase 509, the pressure at the outlet of the pump system is stabilized by imposing corrective movements onto the secondary piston's movement. At the end of the decompression phase 509, the closed loop control is switched off, and during the primary piston's intake phase, the closed loop control remains inactive.

Figure 6:
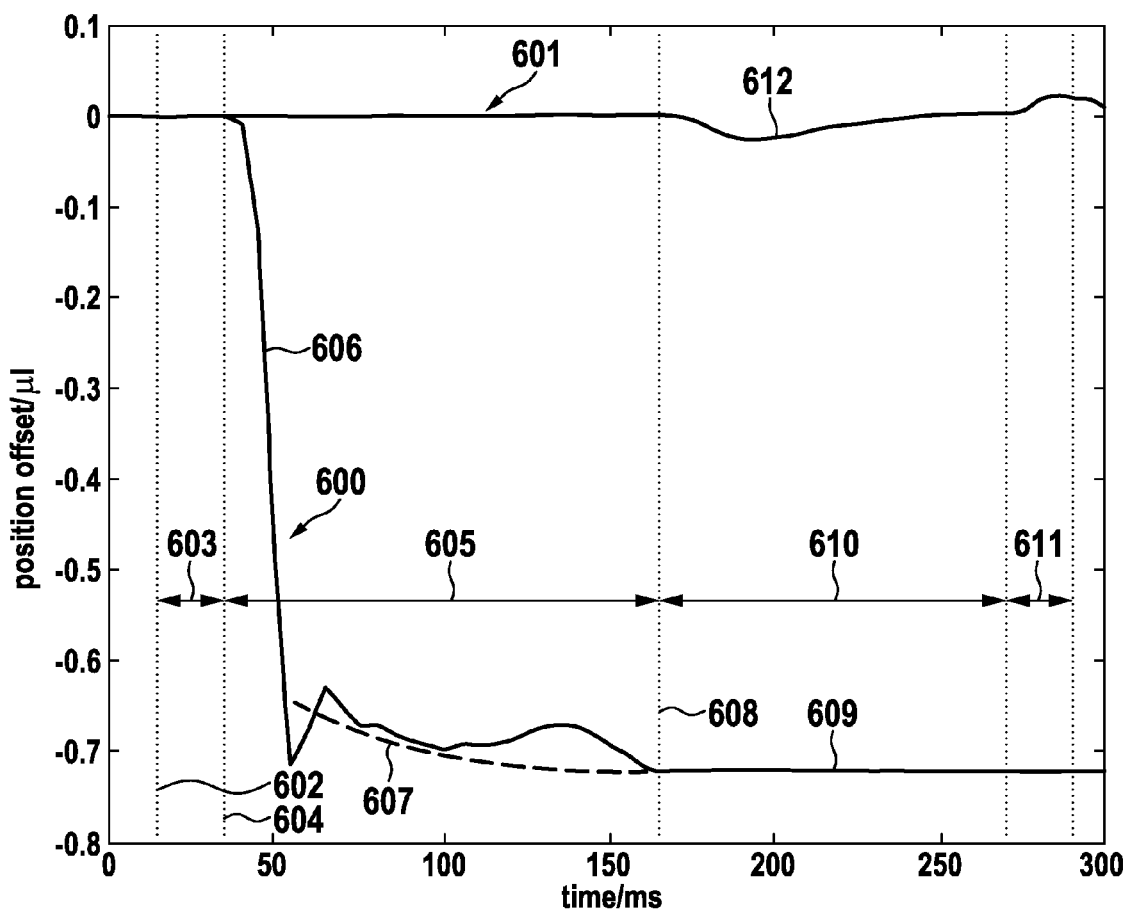
FIG. 6 depicts both the first position correction signal and the second position correction signal as a function of time.

FIG. 6 shows both the first position correction signal 600 for the primary piston pump and the second position correction signal 601 for the secondary piston pump as a function of time, whereby the pump phases indicated in FIG. 6 correspond exactly to the pump phases shown in FIG. 5.

Before the point of time 602, none of the position correction signals 600, 601 is active. Then, during the compression phase 603, the second position correction signal 601 is active. At the point of time 604, the primary piston pump's outlet valve is opened, the second position correction signal 601 becomes inactive, and the first position correction signal 600 becomes active. Then, during the deliver-and-fill phase 605, the closed loop control of the fluid pressure is solely performed by the first position correction signal 600. Hence, during the deliver-and-fill phase 605, the closed loop control is solely applied to the primary piston pump.

In the example shown in FIG. 6, the compression stroke performed during the compression phase 603 has been too short. Therefore, the fluid pressure determined by the pressure detection unit at the point of time 604 is below the desired target value. To drive the fluid pressure towards the desired target pressure, the first position correction signal 600 imposes an additional downward displacement 606 onto the primary piston's regular movement. This additional downward displacement 606 may be seen as an extension of the compression stroke performed during the compression phase 603.

Both the compression stroke performed during the compression phase 603 and the additional downward displacement 606 cause a temperature increase of the fluid contained in the primary piston pump. Hence, after the fluid has been compressed, the fluid's temperature is increased. Now, temperature relaxation processes take place, and the fluid slowly cools down, which leads to a corresponding volumetric contraction of the volume of fluid in the primary piston pump.

To compensate for the thermal contraction of the volume of fluid, the first position correction signal 600 shows a slow decline, which is indicated by the dashed line 607. The slow decline of the first position correction signal 600 superimposes an additional downward movement onto the primary piston's regular movement. The additional downward movement compensates for the slow thermal contraction of the volume of fluid and stabilizes the fluid pressure at the outlet of the pump system.

At the point of time 608, the deliver-and-fill phase 605 is finished, and the closed loop control is switched from the primary piston pump back to the secondary piston pump. Accordingly, at the point of time 608, the first position correction signal 600 becomes inactive, as indicated by the straight line 609, and the second position correction signal 601 is activated. During the outlet valve settle phase 610 and the decompression phase 611, the closed loop control of the fluid pressure at the pump system's outlet is solely performed by the second position correction signal 601. For example, corrective movements 612 of the secondary piston may compensate for thermal effects or for errors that occur when closing the outlet valve. After the decompression phase 611, the second position correction signal 601 becomes inactive.

According to a preferred embodiment of the invention, the information contained in the first position correction signal 600 and the second position correction signal 601 may be used for modifying the regular piston movements of the primary and the secondary piston in subsequent pump cycles. The first position correction signal 600 and the second position correction signal 601 contain information about the deviation between the required piston movements and the regular piston movements. From the first position correction signal 600 and the second position correction signal 601, information about the errors of the regular piston movements may be derived, and said information may be used for modifying the regular piston movements. As a result, in subsequent pump cycles, the extent of required corrections is reduced.

For example, in the example shown in FIG. 6, the compression stroke has been too small, and therefore, it has been necessary to impose an additional downward movement 606 onto the primary piston's movement. The additional downward movement 606 indicates that the compression stroke defined in the regular piston movement is too small. In fact, the additional downward movement 606 may be seen as an extension of the regular compression stroke performed during the compression phase 603. Therefore, the additional downward movement 606 can be used as an indication showing how to adapt the regular piston movement in a way that during the following pump cycles, the magnitude of the correction signals will be reduced. In particular, during the next pump cycle, the regular compression stroke may be extended, which means that the additional downward movement is added to the regular compression stroke. As a consequence, during the next and all the following pump cycles, the magnitude of the correction signals will be reduced.

In addition to the additional downward movement 606 shown in FIG. 6, also the slow additional downward movement that is employed for counteracting the thermal contraction of the volume of fluid in the primary pump chamber may be used for modifying the regular piston movements. In particular, by including the additional slow downward movement into the regular piston movement of the primary piston, the magnitude of the corrective movements imposed during the next pump cycles can be further reduced.

Figure 7:
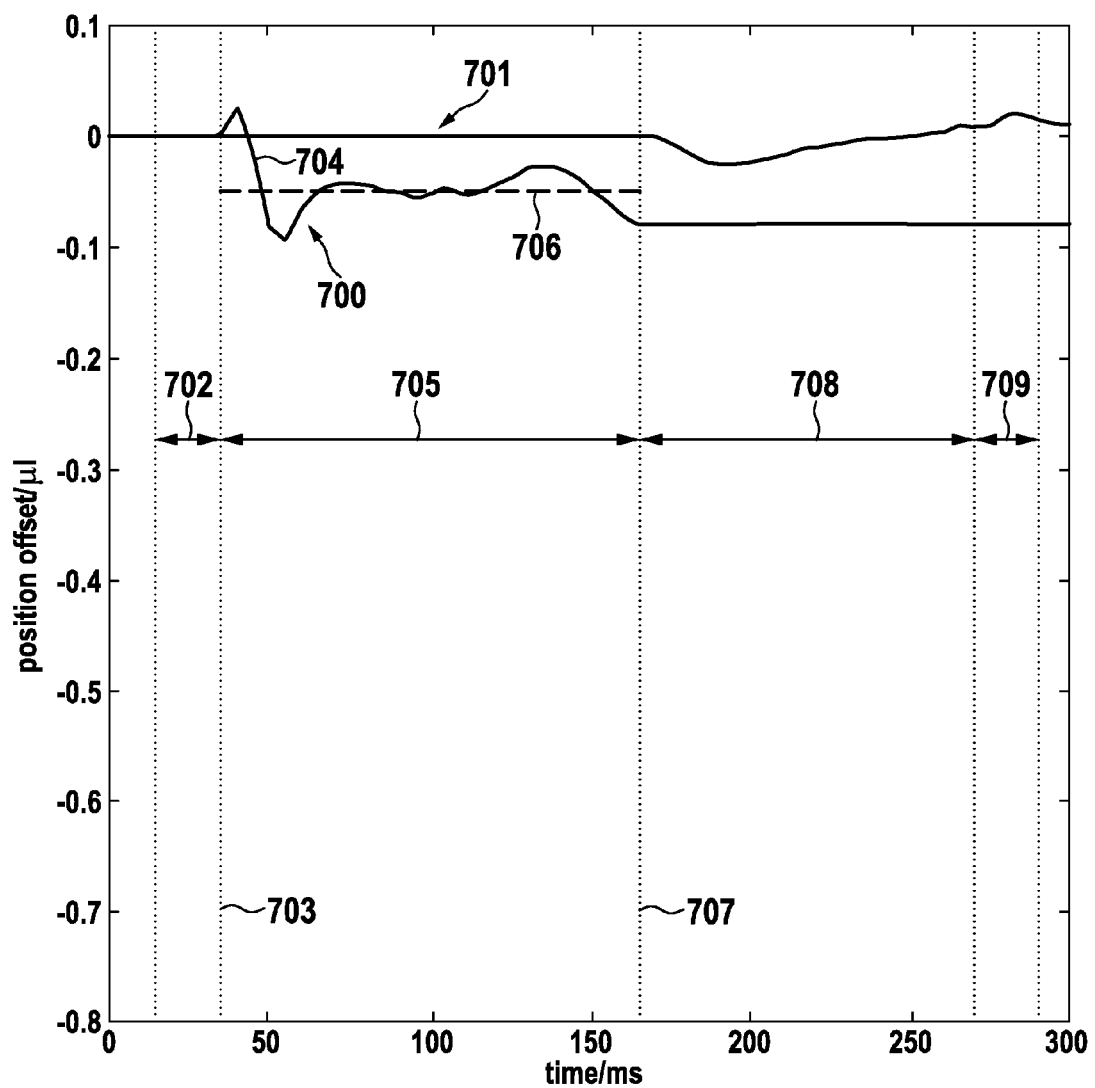
FIG. 7 shows the first position correction signal and the second position correction signal after a modification of the regular piston movements.

By modifying the regular piston movements of the primary and the secondary piston, the corrections imposed by the position correction signals can be reduced during the next and all the following pump cycles. This is shown in FIG. 7. FIG. 7 shows both the first position correction signal 700 and the second position correction signal 701 during a subsequent pump cycle, which occurs after the regular piston movements of the primary and the secondary piston pump have been modified.

During a compression phase 702, a compression stroke is performed, with the closed loop control being applied to the secondary piston pump. At the point of time 703, the compression phase 702 is finished, and the closed loop control is transferred from the secondary piston pump to the primary piston pump. The first position correction signal 700 is activated, whereas the second position correction signal 701 becomes inactive.

At the point of time 703, the pressure measured at the pump system's outlet is still smaller than system pressure, and therefore, an additional downward movement 704 is imposed onto the primary piston's movement.

However, as shown in FIG. 7, the additional downward movement 704 is significantly smaller in magnitude than the corresponding additional downward movement 606 shown in FIG. 6, because in the meantime, the magnitude of the compression stroke of the primary piston pump's regular piston movement has been modified. In particular, the compression stroke of the primary piston pump's regular piston movement has been increased, and therefore, the magnitude of the additional downward movement 704 is decreased.

Furthermore, also the slow decline of the first position correction signal 600, which is indicated by the dashed line 607 in FIG. 6, has been used for modifying the primary piston pump's regular piston movement. As a result, in the first position correction signal 700 shown in FIG. 7, the slow decline is no longer present. Instead, during the deliver-and-fill phase 705, the first position correction signal 700 is substantially kept constant, as indicated by the dashed line 706. The reason is that the thermal contraction has already been considered in the primary piston pump's regular piston movement.

At the point of time 707, the deliver-and-fill phase 705 is finished, and the closed loop control is handed over to the secondary piston pump. During the outlet valve settle phase 708 and the decompression phase 709, the second position correction signal 701 is activated, and the closed loop control is applied to the secondary piston pump.

Hence, as a result of transferring corrective movements to the regular piston movements, the extent of the corrections applied according to FIG. 7 is considerably smaller than the extent of the corrections shown in FIG. 6.

The invention claimed is:

1. A pump unit comprising:
    a primary piston pump with a primary piston and a secondary piston pump with a secondary piston, the primary piston pump being fluidically connected with the secondary piston pump, the pump unit operating periodically according to a pump cycle comprising a compression stroke of the primary piston and a subsequent deliver-and-fill phase for delivering fluid from the primary piston pump to the secondary piston pump and to a fluidic system located downstream of the pump unit;
    a pressure detection unit configured for determining a fluid pressure of fluid dispensed by the pump unit at an outlet of the secondary piston pump; and
    a control unit configured for switching closed loop control between controlling a position of the secondary piston in dependence on the fluid pressure determined by the pressure detection unit during the compression stroke, while a predefined position-versus-time curve is performed by the primary piston, and controlling a position of the primary piston in dependence on the fluid pressure determined by the pressure detection unit during the deliver-and-fill phase, while a predefined position-versus-time curve is performed by the second piston.

2. A fluid separation system for separating compounds of a sample fluid in a mobile phase, the fluid separation system comprising:
    a pump unit according to claim 1, the pump unit being configured for driving the mobile phase through the fluid separation system; and
    a separation unit configured for separating compounds of the sample fluid in the mobile phase.

3. The fluid separation system of claim 2, further comprising at least one of:
    a sample injector configured for introducing the sample fluid into the mobile phase;
    a detector configured for detecting separated compounds of the sample fluid;
    a collection unit configured for collecting separated compounds of the sample fluid;
    a data processing unit configured for processing data received from the fluid separation system; and
    a degassing apparatus configured for degassing the mobile phase.

4. The fluid separation system of claim 2, wherein the separation unit comprises a chromatographic column.

5. A method for controlling operation of a pump unit, the pump unit comprising a primary piston pump having a primary piston and a secondary piston pump having a secondary piston, the primary piston pump being fluidically connected with the secondary piston pump, the primary piston pump comprising an inlet valve and an outlet valve, and the pump unit operating periodically according to a pump cycle, the method comprising:
  detecting a fluid pressure of fluid dispensed by the pump unit at an outlet of the secondary piston pump;
  during a first time interval of the pump cycle, comprising a deliver-and-fill phase, performing closed loop control to control a position of the primary piston in dependence on a detected fluid pressure, while the secondary piston follows a corresponding predefined position-versus-time curve; and
  during at least one second time interval of the pump cycle, switching the closed loop control to control a position of the secondary piston in dependence on the detected fluid pressure, while the primary piston follows a corresponding predefined position-versus-time curve.

6. The method of claim 5, wherein controlling the position of the primary piston using the closed loop control comprises:
  determining a variance between the detected fluid pressure of the fluid dispensed by the pump unit and a predetermined target pressure, and deriving, from said variance, a first position correction signal for imposing a corrective movement onto a regular piston movement of the primary piston.

7. The method of claim 5, wherein during the first time interval, when the detected fluid pressure of the fluid dispensed by the pump unit is too small, movement of the primary piston is corrected by superimposing a forward movement onto the primary piston, and when the detected fluid pressure of the fluid dispensed by the pump unit is too large, movement of the primary piston is corrected by superimposing a backward movement onto the primary piston.

8. The method of claim 5, wherein controlling the position of the secondary piston using the closed loop control comprises:
  determining a variance between the detected fluid pressure of the fluid dispensed by the pump unit and a predetermined target pressure, and deriving, from the variance, a second position correction signal for imposing a corrective movement onto a regular piston movement of the secondary piston.

9. The method of claim 5, wherein, during the first time interval, said closed loop control of the position of the primary piston is performed in a way that the fluid pressure of the fluid dispensed by the pump unit continues to follow its former trend.

10. The method of claim 5, wherein, during the first time interval, said closed loop control of position of the primary piston is performed in a way that the fluid pressure of the fluid dispensed by the pump unit is driven towards or substantially kept at a predetermined target pressure.

11. The method of claim 10, further comprising at least one of:
  the target pressure is determined by performing an extrapolation of former values of the fluid pressure of the fluid dispensed by the pump unit; and
  the target pressure is determined by performing an extrapolation of former values of the fluid pressure of the fluid dispensed by the pump unit in a way that the fluid pressure of the fluid dispensed by the pump unit shows a continuous progression.

12. The method of claim 5, wherein the second time interval comprises a compression stroke phase of the primary piston in the pump cycle.

13. The method of claim 12, wherein the inlet valve and an outlet valve of the primary piston pump are closed during the compression stroke phase, and wherein the outlet valve of the primary piston pump opens at the start of the delivery and fill phase.

14. The method of claim 5, wherein the second time interval comprises an outlet valve settle phase in the pump cycle for closing the outlet valve of the primary piston.

15. The method of claim 14, further comprising:
  during a subsequent decompression stroke of the primary piston in the pump cycle, continuing to perform the closed loop control to control the position of the secondary piston in dependence on the detected fluid pressure, while the primary piston follows a corresponding predefined position-versus-time curve.

16. The method of claim 15, further comprising:
  during a subsequent intake phase of the primary piston in the pump cycle, performing no closed loop control on the primary piston and the secondary piston.

17. The method of claim 5, further comprising:
  deriving, from the closed loop control the position of the primary piston performed during the first time interval, at least one correction to be applied to a regular piston movement of at least one of the primary piston pump and the secondary piston pump, with the at least one correction being used for modifying a regular piston movement of at least one of the primary piston pump and the secondary piston pump during at least one subsequent pump cycle.

18. The pump unit of claim 1, wherein the control unit is further configured for switching the closed loop control to controlling the position of the secondary piston in dependence on the fluid pressure determined by the pressure detection unit during a subsequent outlet valve settle phase in the pump cycle, when an outlet valve of the primary piston pump is closing, while a predefined position-versus-time curve is performed by the primary piston.

19. The pump unit of claim 18, wherein the control unit is further configured for performing no closed loop control of the primary piston and the secondary piston during a subsequent intake phase of the primary piston in the pump cycle.

* * * * *

UNITED STATES PATENT AND TRADEMARK OFFICE
CERTIFICATE OF CORRECTION

PATENT NO. : 8,182,680 B2  
APPLICATION NO. : 12/431972  
DATED : May 22, 2012  
INVENTOR(S) : Philip Herzog et al.

Page 1 of 1

It is certified that error appears in the above-identified patent and that said Letters Patent is hereby corrected as shown below:

In column 13, line 56, in Claim 10, delete "of position" and insert -- of the position --, therefor.

Signed and Sealed this  
Third Day of July, 2012

David J. Kappos  
*Director of the United States Patent and Trademark Office*